United States Patent [19]

Kawashima et al.

[11] Patent Number: 4,954,465
[45] Date of Patent: Sep. 4, 1990

[54] APPARATUS FOR REMOVING STINK

[75] Inventors: Masaei Kawashima, Fujiokamachi; Reishi Naka; Teruo Tsunoda, both of Ohiramachi; Nobuyoshi Suenaga, Oyama; Syozo Ogawa, Ohiramachi; Masaaki Kashiwabuchi, Tochigi; Miyakichi Kameda, Sano; Koosuke Tanaka, Ohiramachi, all of Japan

[73] Assignee: Hitachi, Ltd., Tokyo, Japan

[21] Appl. No.: 295,754

[22] Filed: Jan. 11, 1989

[30] Foreign Application Priority Data

Jan. 22, 1988 [JP] Japan .................................. 63-10601
Jan. 22, 1988 [JP] Japan .................................. 63-10602

[51] Int. Cl.$^5$ .............................................. B01J 37/34
[52] U.S. Cl. ................................... 502/5; 62/264; 502/182; 502/183; 502/417
[58] Field of Search ...................... 62/264; 502/5, 182, 502/183, 417

[56] References Cited

U.S. PATENT DOCUMENTS

| 2,988,432 | 6/1961 | Long | 62/264 |
| 3,231,513 | 1/1966 | Graves | 502/5 |
| 3,658,724 | 4/1972 | Stiles | 502/183 |
| 3,683,638 | 8/1972 | Devon | 62/264 |
| 3,799,250 | 3/1974 | Dyre | 62/264 |
| 3,890,245 | 6/1975 | Berg et al. | 502/5 |
| 4,125,482 | 11/1978 | Sinha | 502/417 |
| 4,322,394 | 3/1982 | Mezey et al. | 502/5 |

FOREIGN PATENT DOCUMENTS

| 0125601 | 7/1983 | Japan | 502/5 |
| 0203701 | 11/1984 | Japan | 502/5 |
| 3078739 | 4/1988 | Japan . | |

Primary Examiner—Ronald C. Capossela
Attorney, Agent, or Firm—Antonelli, Terry, Stout & Kraus

[57] ABSTRACT

A photocatalystic decomposing apparatus comprises absorbent including honeycomb form active carbon and titanium oxide acting as photocatalyst applied to a surface of the active carbon, and a light source for generating ultraviolet rays exciting the photocatalyst. Stink ingredient is absorbed to the active carbon by passing air flow through openings in the honeycomb, and the absorbed stink ingredient is decomposed by exciting the photocatalyst due to application of the ultraviolet rays.

7 Claims, 13 Drawing Sheets

APPARATUS FOR REMOVING STINK

BACKGROUND OF THE INVENTION

The present invention relates to an apparatus for removing and decomposing stink, and more particularly, it relates to an apparatus for removing and decomposing stink which utilizes absorbent having photocatalyst.

In a conventional stink removing apparatus, for example, as disclosed in the Japanese Utility Model Laid Open Publication No. 47-22566, a casing containing absorbent such as active carbon was inserted into an air flow passage, thereby removing stink ingredient entrained by the air by absorbing it into the absorbent.

As mentioned above, since the conventional stink removing apparatus operates to remove the generated stink by absorbing it into the absorbent such as the active carbon, there arose a problem that the stink ingredient having high density could not be removed in a short time. Further, since an amount of the stink ingredient absorbed by the absorbent (i.e., holding ability of the absorbent) is limited, it was necessary to replace or reproduce the absorbent after it was used for a predetermined time period.

SUMMARY OF THE INVENTION

An object of the present invention is to provide an apparatus for removing stink, which can stably maintain an ability of removal of stink for a long time by refleshing absorbent all the way.

The above-mentioned object is achieved by providing a layer of photocatalyst, which can decompose stink ingredient sticked or absorbed on the absorbent by the action of light, on a surface of the absorbent, and by radiating exciting light (for exciting the photocatalyst) onto the photocatalyst from a light source, and by exciting the photocatalyst.

According to the stink removing apparatus of the present invention, light having energy higher than that of a band gap of the photocatalyst is radiated onto the photocatalyst provided on the surface of the absorbent to excite the photocatalyst. Consequently, decomposition of the stink ingredient is caused in the photocatalyst so that the stink ingredient absorbed or sticked to the absorbent is gradually decomposed and removed from a surface of the absorbent. When the photocatalyst exciting light source comprises a light source which hardly generates heat, the stink ingredient is gradually decomposed and removed from the surface of the absorbent mainly due to diffusion action caused by a difference in density between an outer portion and an inner portion of the absorbent. On the other hand, when the photocatalyst exciting light source comprises a light source which generates heat, since the absorbent is situated near the light source, the absorbent is heated to reduce the holding ability thereof, thus releasing the stink ingredient while decomposing it effectively by the photocatalyst on the absorbent.

DETAILED DESCRIPTION OF THE PREFERRED EMBODIMENTS

First of all, the present invention will be explained in connection with a preferred embodiment thereof with reference to FIGS. 1 to 5.

Figure 2:
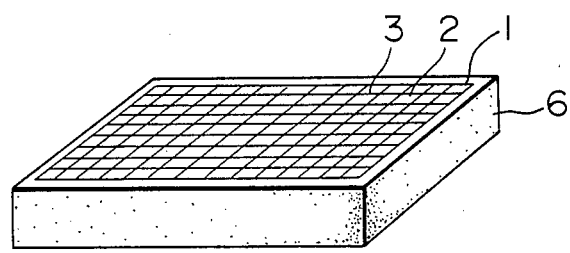
FIG. 2 is a perspective view of a stink removing apparatus according to another embodiment of the present invention.

An absorbent (for example, active carbon) 1 is configurated as a honeycomb form to increase a surface area thereof, and thus has a plurality of honeycomb form apertures 2. Photocatalyst 3 is provided on a surface of the honeycomb form absorbent. The photocatalyst 3 may be mixed and kneaded with the absorbent 1. In this embodiment, an exciting source 4 for exciting the photocatalyst comprises an ultraviolet ray lamp mounted on a socket 5. As shown in FIG. 2, the honeycomb form absorbent 1 may be encircled by a buffer band 6 which may be made of, for example sponge buffer material. When the absorbent is configured in the honeycomb form, since the periphery of the absorbent often becomes fragile or brittle, the buffer band 6 may be arranged around the absorbent to prevent the absorbent from damaging due to impact.

Figure 1:
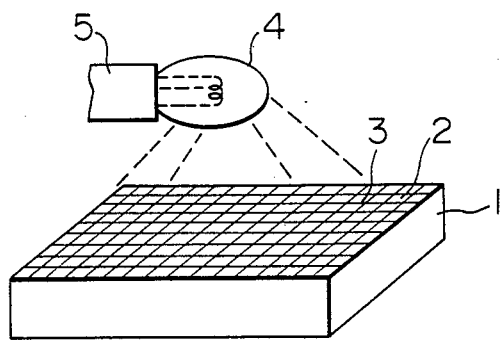
FIG. 1 is a perspective view of a stink removing apparatus according to a preferred embodiment of the present invention.
Figure 3:
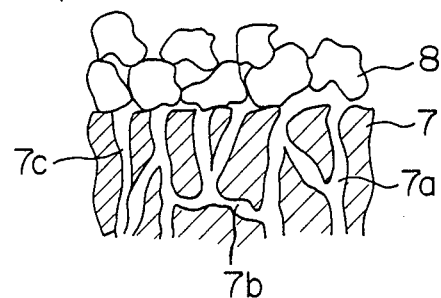
FIG. 3 is an enlarged sectional view of a portion of the apparatus of FIG. 1.

FIG. 3 is an enlarged view of a portion of FIG. 1, showing the absorbent comprising the honeycomb form active carbon and particles of the photocatalyst comprising metallic oxide existing on the surface of the absorbent. In FIG. 3, a reference numeral 7 designates the active carbon as a base material for the absorbent, which includes a plurality pores 7a, 7b and 7c each having a dimension of the order of a few ten angstrom. A number of particles 8 of the photocatalyst are adhered to the surface of the active carbon 7. Each of these particles normally has a diameter of the order of a few hundred angstrom, and thus is larger than the diameter of the pore 7a 7c in the active carbon by about ten times; however, the particles are so selected as not to close or shut off the pores in the active carbon.

Figure 4:
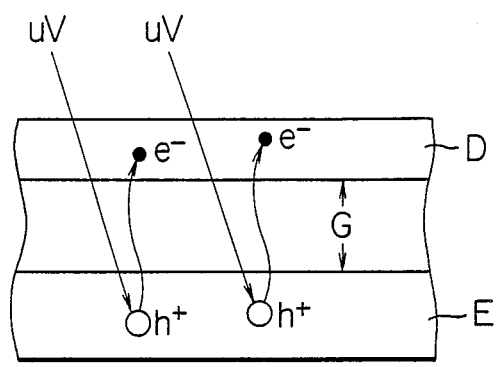
FIG. 4 is an explanatory view for explaining a principle of action of photocatalyst.

Next, the action of the photocatalyst will be explained. The photocatalyst is a substance which can convert photo energy into chemical energy, and the particles of the metallic oxide constituting the photocatalyst are semi-conductor and each has a charged band E, a conductor band D, and a band gap G therebetween, as shown in FIG. 4. The band gap has a value inherent to the photocatalyst. For example, when the photocatalyst comprises titanium dioxide, the band gap is 3 eV. When light having a wavelength shorter than about 413 nm is applied onto the titanium dioxide, electrons in the charged band E are flying onto the conductor band D, thus creating positive holes $h^+$ where the electrons $e^-$ are left. This condition corresponds to an excited condition of the photocatalyst. When the photocatalyst comprises the titanium dioxide, such excited condition is created as the ultraviolet rays (wavelength is 254 nm, input is 2 watts) are applied onto the titanium dioxide.

OH-radical is generated from the surface of the photocatalyst or semi conductor in such excited condition, as shown in the following reaction formula:

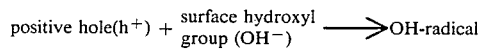

This OH-radical acts as active species to oxidize and decompose the stink ingredient. In this case, decomposible component in the stink ingredient is decomposed before it is absorbed by the active carbon 7; on the other hand, non-decomposible component (i.e., component slowly decomposed) in the stink ingredient is absorbed by the active carbon and is condensed therein, and thereafter, it is gradually decomposed from the surface of the active carbon by the particles 8 of the photocatalyst. Accordingly, it is effective to position a bright point of the photocatalyst exciting light source in the proximity of a position where density of absorbed stink ingredient on the absorbent is the thickest or highest. For example, when the light source is energized (applied) for 20-40 minutes, a distance between the bright point of light and the absorbent may be about 1.5 cm-5 cm. Further, for example, when the stink ingredient, particularly methyl mercaptan ($CH_3SH$) known as most bad smell ingredient absorbed to the absorbent by a Van der Waals force is oxidized and decomposed, the oxidation decomposition will be caused by the following chemical reaction to eliminate the bad smell;

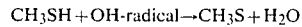

Figure 5:
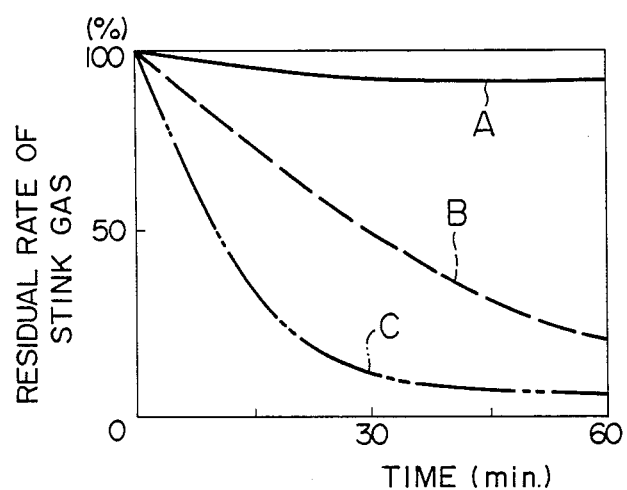
FIG. 5 is a graph showing a feature for explaining the effect of the preferred embodiment of the present invention.

The other stink ingredients absorbed to the absorbent can also be decomposed by an oxidation force of the OH radical to eliminate the bad smell. FIG. 5 shows a test result obtained when anatase crystal titanium oxide is used as the photocatalyst and the active carbon is used as the absorbent. FIG. 5 shows residual rate of stink gas, i.e., residual rate of dimethyl sulfide after the dimethyl sulfide of 5 ppm is introduced in a container having an interior volume of 250 l and then the stink removing apparatus is driven. An abscissa indicates "time" and an ordinate indicates "residual rate of stink gas". A solid line A shows a feature of natural decay of the dimethyl sulfide; a broken line B shows a feature of decay in the case where the anatase crystal titanium oxide is applied to the metal plate without using the absorbent and the ultraviolet rays are applied thereon, and a two-dot chain line C shows the effect of the present invention according to one embodiment thereof, that is, shows a feature of decay in the case where the honeycomb form active carbon is used as the absorbent and the anatase crystal titanium oxide is applied to the surface of the active carbon and the ultraviolet rays are applied thereon. As seen from the feature of decay shown by the broken line B, the density of stink ingredient can be reduced by decomposing the stink ingredient, even when the photocatalyst is used alone. It has been found that, when the absorbent was used, since the stink ingredient could be collected to the absorbent and decomposed, the speed of decomposition of the stink ingredient was increased. The decomposition may be continuously performed by energizing the ultraviolet ray lamp while providing the stink ingredient flow, or may be intermittently performed by energizing the ultraviolet ray lamp after the stink ingredient is collected to the absorbent because the stink ingredient can be quickly collected by the Van der Waals force of the absorbent. When the honeycomb form active carbon is used as the absorbent (two-dot chain line C), since the honeycomb active carbon does not include any organic bodies due to high burning temperature thereof (about 1000° C.), the active carbon with the application of the ultraviolet rays can be fully practically used.

Figure 7:
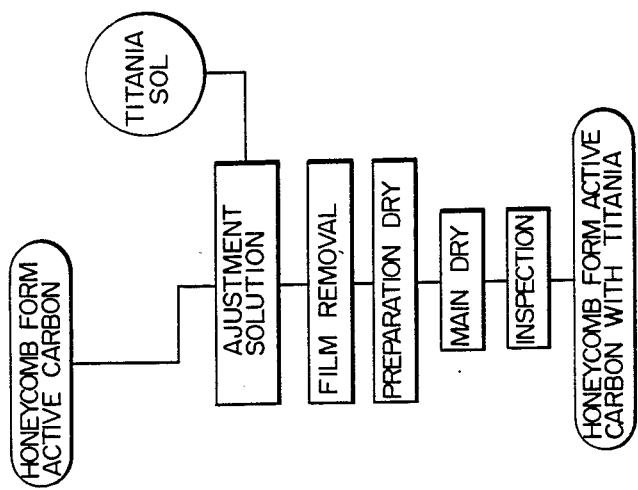
FIG. 7 is a flow chart showing a process for applying the photocatalyst onto a surface of the honeycomb form active carbon.
Figure 6:
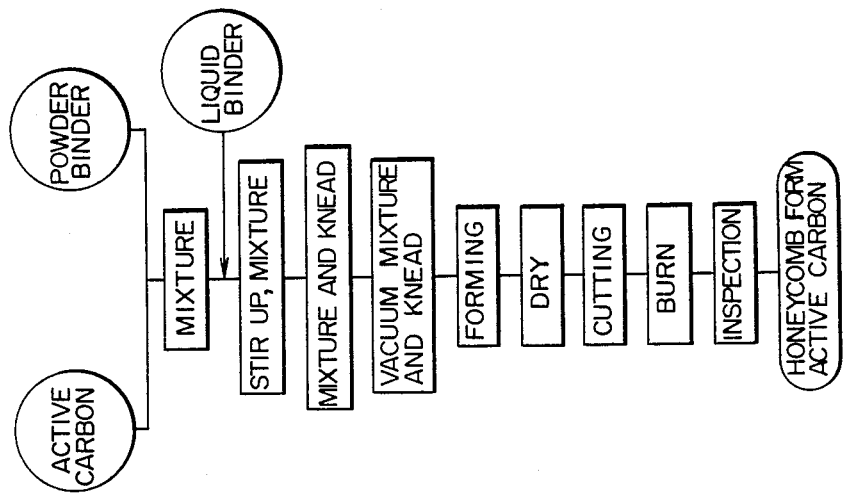
FIG. 6 is a flow chart showing a process for manufacturing a honeycomb form active carbon.

FIG. 6 shows the manufacturing process for the honeycomb active carbon. On the other hand, FIG. 7 shows a process for immersing the honeycomb form active carbon into titania sol having the anatase crystal (for example, solution of titanium dioxide having particle diameter of about 50 nm and formed as sol condition) and then applying anatase crystal titania particles (i.e., photocatalyst) to the surface of the honeycomb form active carbon. The absorbent is not limited to the honeycomb form active carbon, but may comprises zeolite, porous ceramics, or silica gel as far as it has absorbing ability. Similarly, the photocatalyst is not limited to the anatase crystal titanium oxide, but may comprise simple substance or composite of metallic oxide such as titanium oxide, tungsten oxide or zinc oxide. The exciting source for exciting the photocatalyst must provide the energy more than the band gap inherent to the photocatalyst, as shown in the following Table 1:

TABLE 1

| Band Gap of Semi conductor and Wavelength of Light corresponding thereto | | |
|---|---|---|
| Semi-conductor | Band Gap Energy | Excited Wavelength of Light |
| Titanium Oxide ($TiO_2$) | $3.0^{eV}$ | $413^{nm}$ |
| Tungsten Oxide ($Wo_3$) | 2.8 | 443 |

TABLE 1-continued

Band Gap of Semi conductor and Wavelength of Light corresponding thereto

| Semi-conductor | Band Gap Energy | Excited Wavelength of Light |
|---|---|---|
| Di-iron Trioxide ($Fe_2O_3$) | 2.2 | 564 |
| Assenical Gallium (GaAs) | 1.4 | 886 |
| Molybdenum Sulfide ($MoS_2$) | 1.2 | 1033 |

Since the removeal ability is more improved by increasing the surface area of the absorbent, the configuration of the absorbent may be sponge form, net form, concentric circular form, concentric rectangular form or the like, other than the honeycomb form, and may be suitably selected in accordance with equipments on which the absorbent is mounted. Further, the particle diameter of the photocatalyst applied on the surface of the absorbent not to reduce the absorbing ability of the absorbent may be sufficiently larger than the dimension of the pores in the absorbent.

Figure 11:
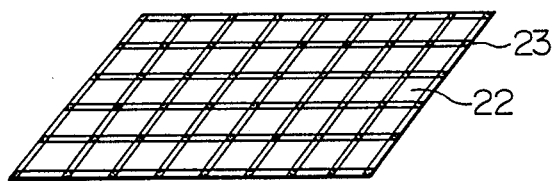
FIGS. 11 to 14 are perspective views showing other various forms or shapes of the active carbon, respectively.
Figure 12:
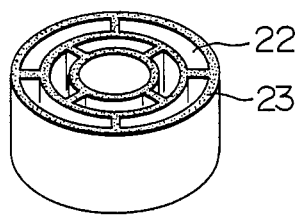
Figure 13:
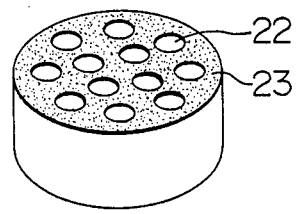
Figure 14:
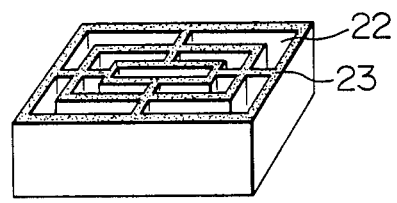

Incidentally, the configuration of the absorbent is not limited to the above-mentioned forms, but may be selected from any forms such as fibre form, plate form, particle form or the like, as far as the photocatalyst exciting light can be applied on the photocatalyst of the absorbent. For example, the absorbent with the photocatalyst may be net form one utilizing fibre active carbon as shown in FIG. 11, concentric circular form one as shown in FIG. 12, cylindrical or prismatic form one having a plurality of through holes as shown in FIG. 13, or concentric rectangular form one as shown in FIG. 14. In these drawings, a reference numeral 22 designates a plurality of through holes or openings, and 23 designates the absorbent with the photocatalyst. When the absorbent is mounted on the stink removing apparatus, the absorbents each having the same form or the absorbent having the different forms selected from the above mentioned forms such as the honeycomb form, net form, concentric rectangular form and the like can be optionally used.

Further, when the metallic oxide such as the titanium oxide is used as the photocatalyst, the photocatalyst can also be utilized as the absorbent. That is to say, a porous molded product having the absorbing ability can be obtained by burning and molding metallic oxide which can constitute the photocatalyst. In this case, it should be understood that there is no need to use the different absorbent.

Figure 8:
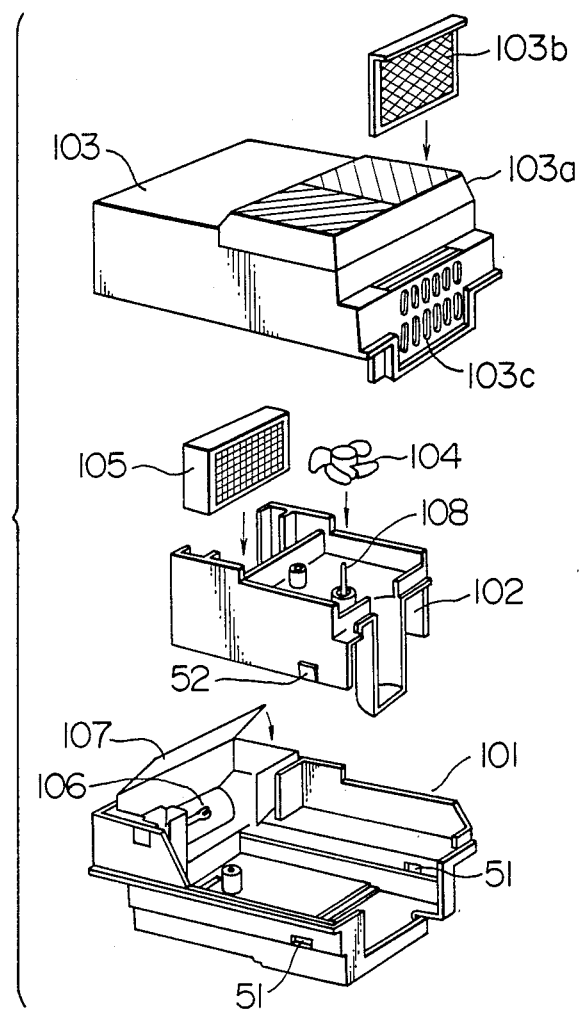
FIG. 8 is an exploded perspective view showing an example of a concrete construction of the stink removing apparatus according to the present invention.

Now, FIG. 8 shows an example of a concrete construction of the stink removing apparatus according to the present invention.

Figure 9:
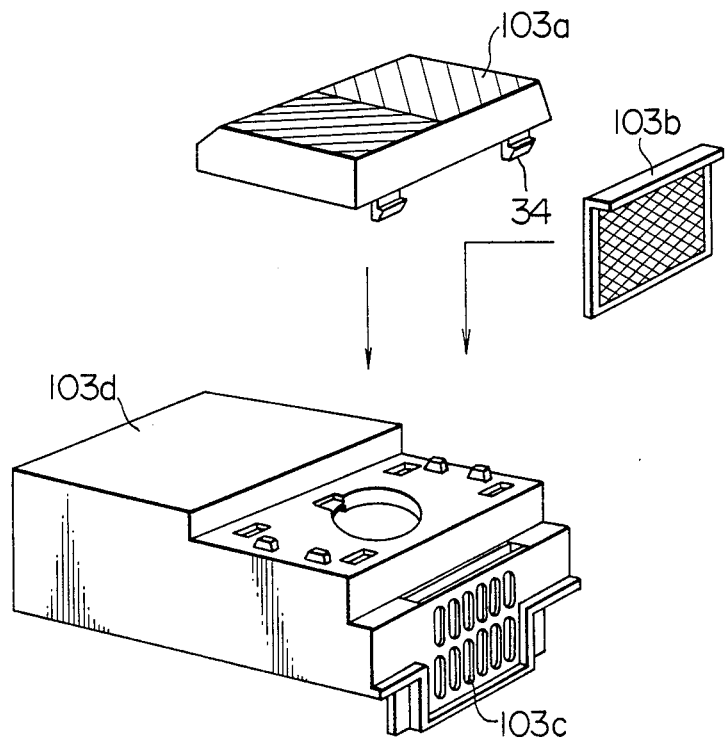
FIG. 9 is a perspective view showing a main portion of the apparatus of FIG. 8.

As shown in FIG. 8, the apparatus comprises a lower cover 101, an intermediate partition 102 and an upper cover 103, which can be made of plastic or metallic material and by which a body of the stink removing apparatus is constituted. The stink ingredient is passed through the apparatus by means of a blower fan 104. In this way, the stink ingredient is absorbed and eliminated by the apparatus. The apparatus also includes a photocatalyst exciting light source such as an ultraviolet ray lamp 106, and an ultraviolet reflecting plate 107 made of aluminum material. Arrows shown in FIG. 8 indicate assembling directions in assembling the elements as the stink removing apparatus. In the assembling operation, first of all, pawls 52 formed on the intermediate partition 102 are introduced into corresponding pawl receiver openings 51 formed in the lower cover 101. Then, a stink removing element 105 and the blower fan 104 are assembled to the intermediate partition 102 and a fan motor 108, respectively. Thereafter, the upper cover 103 is assembled to the lower cover 101. As shown in FIG. 9, the upper cover 103 is constituted by a body of the upper cover 103d, a fan cover 103a, and a pre-filter 103b to improve molding ability and assembling ability. The body of the upper cover 103d includes a plurality of intake openings 103c. Arrows shown in FIG. 9 indicate assembling directions in assembling the fan cover 103a and the pre-filter 103b into the body 103d of the upper cover 103. The assembling operation is completed by attaching the fan cover 103a to the upper cover body 103d through pawls 34 and inserting the pre-filter 103b into the upper cover body 103d.

Figure 10:
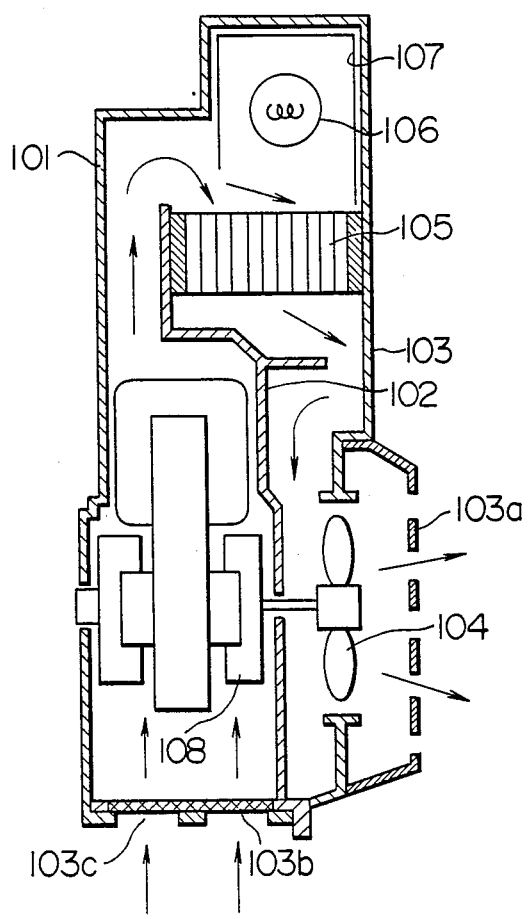
FIG. 10 is a longitudinal sectional view of the apparatus of FIG. 8 for explaining an air flow passing therethrough.

Next, an air flow in the stink removing apparatus as constructed above will be explained with reference to FIG. 10 showing a longitudinal sectional view of the apparatus. In FIG. 10, arrows indicate directions of the air flow which is flowing through an air passage defined by plastic or metallic material. The air stream is introduced from the intake openings 103c through the pre-filter 103b by rotating the blower fan 104 by means of a fan motor 108. Thus, relatively large dust in the air stream is removed by the pre-filter 103b. Thereafter, the air stream is passed through the stink removing element (absorbent) 105, where the stink ingredient in the air stream is removed, and then, the air stream is discharged or exhausted from the fan cover 103a. Since the blower fan 104 is constituted by an exhaust fan, the air stream introduced through the intake openings 103c becomes a even flow, thus reducing flowing resistance in comparison with that of air stream caused by a forced draft fan. Further, since the blower fan 104 and fan motor 108 are spaced apart from the ultraviolet ray lamp 106, the fan 104 and fan motor 108 are not influenced upon heat and/or ultraviolet rays from the lamp 106.

Next, the decomposing operation by means of the stink removing apparatus according to the embodiment of the present invention will be explained, on the basis of the air flow mentioned above, with reference to FIG. 15 (where an abscissa indicates "time" and an ordinate indicates "items" of operating elements or matters).

Figure 15:
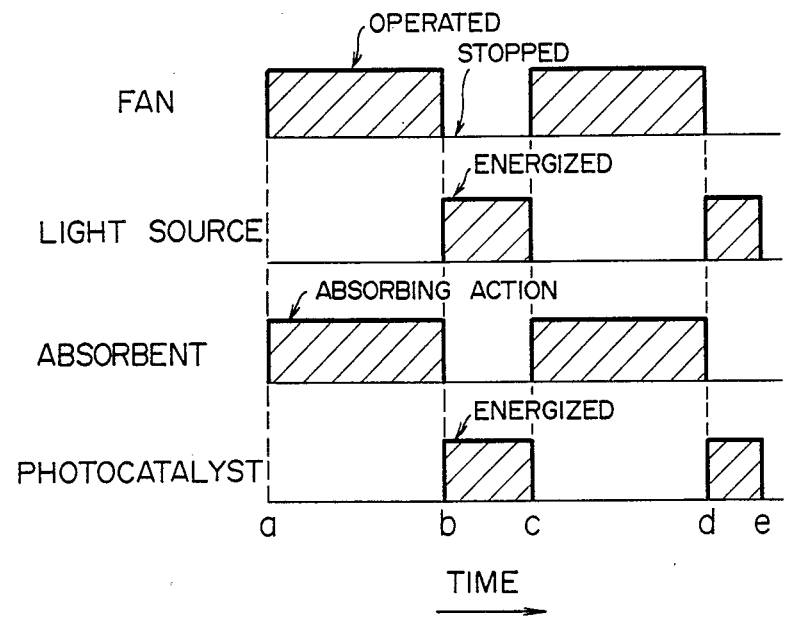
FIG. 15 is an explanatory view for explaining an operation of the stink removing apparatus according to the present invention.

In FIG. 15, a indicates a starting for the blower fan; a time interval between a and b corresponds to a period when the fan is being operated and the absorbing action is effected; a time interval between b and c corresponds to a period when the fan is being stopped and the exciting light source is being energized; a time interval between c and d is a period when the fan is being operated again and the absorbing actions is effected again; and a time interval between d and e is a period when the fan is being stopped again and the exciting light source is being energized again.

Normally, the stink ingredient is removed by being absorbed to the absorbent while the air stream caused by the blower fan is made to flow through the absorbent 105. Here, in order to clean the absorbent in the following manner, the blower fan 104 is stopped and the ultraviolet ray lamp 106 is energized. That is to say, the stink ingredient absorbed by the honeycomb form active carbon is gradually floated on the outer surface of the active carbon by the heat as well as the ultraviolet rays generated by the ultraviolet ray lamp 106. In this case, the photocatalyst on the surface of the absorbent is in the excited condition by the application of the ultraviolet rays. As an example, when the photocatalyst comprises titanium dioxide, by applying the light having a wavelength of 420 nm or less (mainly, ultraviolet rays), the electrons in the charged band are shifted to the conductor band, thus creating the positive holes in the charged band, as previously stated. Due to such bipolar condition, the chemical reaction is caused in the photocatalyst, thereby decomposing the stink ingredient floated from the honeycomb form active carbon. For example, the hydroxyl group $OH^-$ existing on the surface of the photocatalyst is changed to the OH radical by the above mentioned positive holes, thereby creating the active species to decompose the stink ingredient, with the result that the stink ingredient is changed to low-molecular one to reduce the smell or stink, and thus, is removed as a component which is not likely to be absorbed by the honeycomb form active carbon. Incidentally, as stated above, by stopping the blower fan 109 when the ultraviolet ray lamp 106 is energized, it is possible to effectively make the stink ingredient floated from the honeycomb form active carbon to be contact with the photocatalyst. Further, when the blower fan 109 is stopped, the heat from the ultraviolet ray lamp 106 can be effectively transmitted to the photocatalyst, thus promoting the floating action of the stink ingredient from the honeycomb form active carbon. Further, since the stink ingredient is floated onto the surface of the honeycomb active carbon due to diffusion when the density of the stink ingredient around the surface of the active carbon is lowered, the cleaning operation regarding the honeycomb form active carbon can smoothly be performed.

While not shown in FIG. 15, the similar effect can be obtained by energizing the exciting light source and the fan in synchronous with each other to simultaneously energize the light source and the fan whereby the absorbing action and the decomposing action are simultaneously effected. For example, it is possible to simultaneously energize the light source and the fan when the stink removing apparatus is started to drive and to simultaneously disenergize the light source and the fan when the apparatus is stopped. Further, in the intermittent illumination of the light source, it is possible to optionally select the time interval for illuminating the light source so as to repeat the energization and disenergization of the light source for a predetermined time interval by using an appropriate timer, or to energize the light source for a predetermined time interval once or twice a day. Further, it is also possible to energize the light source, and accordingly, to decompose the stink ingredient in synchronous with a driving mode inherent to the equipments on which the stink removing apparatus is mounted. For example, the stink removing apparatus may be mounted in a refrigerator and the light source may be energized in synchronous with a defrost action for periodically removing the frost grown on a cooler disposed in the refrigerator. Incidentally, when the light source is arranged in the proximity of the absorbent, since the absorbent is heated immediately after the light source is energized, the stink ingredient can be expelled from the absorbent, thus enhancing the cleaning action for the absorbent. According to the tests, it has been found that, when the fan was stopped and the light source was energized, the temperature of the absorbent was higher than the surrounding temperature by about 10° C. sufficient to expel the stink ingredient from the absorbent due to the heat. When output of the light source is increased, the more effective result can be obtained since the temperature of the absorbent is still more increased.

Figure 16:
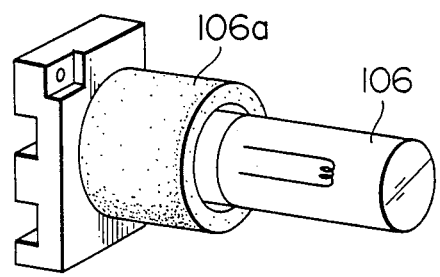
FIG. 16 is a perspective view of an embodiment of a light source for exciting the photocatalyst.

FIG. 16 shows an example of the photocatalyst exciting light source, which includes a small sized ultraviolet ray bulb lamp 106 mounted on a socket cover 106a which is made of porcelainous material to prevent deterioration thereof due to the ultraviolet rays.

Figure 17:
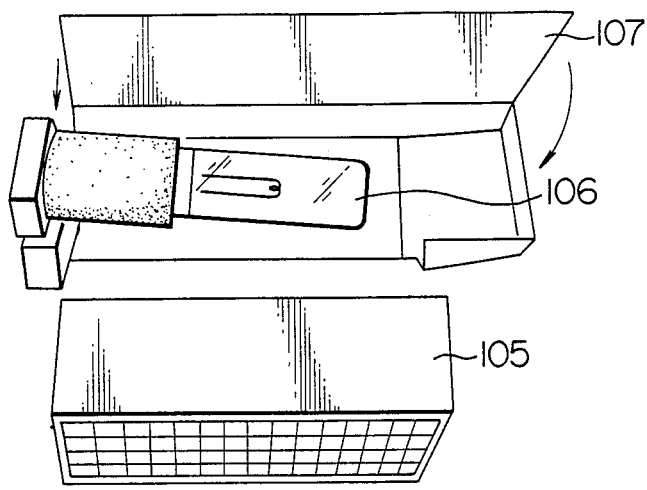
FIG. 17 is a perspective view showing an example of a positional relation between an aluminum reflector plate, the light source and the active carbon.

FIG. 17 shows the positional relation between the absorbent element 105, the ultraviolet ray lamp 106 and the aluminum reflector plate 107. The positional relation is so selected that when the ultraviolet lamp 106 is energized the radiated ultraviolet rays are effectively applied onto the photocatalyst layer on the absorbent 105 and the upper and lower covers 101, 103 are least influenced upon the ultraviolet rays. Incidentally, arrows in FIG. 17 show adjustment of the position of the reflector plate 107.

According to this embodiment of the invention, since the absorbent for absorbing the stink ingredient has the photocatalyst which is applied onto the absorbent or is mixed and kneaded with the absorbent, and the exciting light source for exciting the photocatalyst is arranged in the proximity of the absorbent, the absorbing speed, i.e., the stink removing speed due to the absorbent can be increased, and the stink ingredient absorbed to the absorbent can be continuously or intermittently decomposed due to oxidization, and the absorbing ability of the absorbent can be lengthened, thus providing a maintenance-free stink removing apparatus. By using the simple substance or composite of the metallic oxide such as the titanium oxide, tungsten oxide or zinc oxide as the photocatalyst together with the absorbent, it is possible to decompose the stink ingredient absorbed to the absorbent by mere sunlight or normal visible light due to the photocatalytic action of the metallic oxide. Accordingly, the stink can be removed by the absorbent, and the absorbent having the metallic oxide thereon can be refleshed by exposing it to the sunlight or visible light, whereby the absorbent can be used repeatedly (which was not impossible in the prior techniques).

Next, a concrete example that the stink removing apparatus so constructed is mounted in the refrigerator will be explained.

Figure 18:
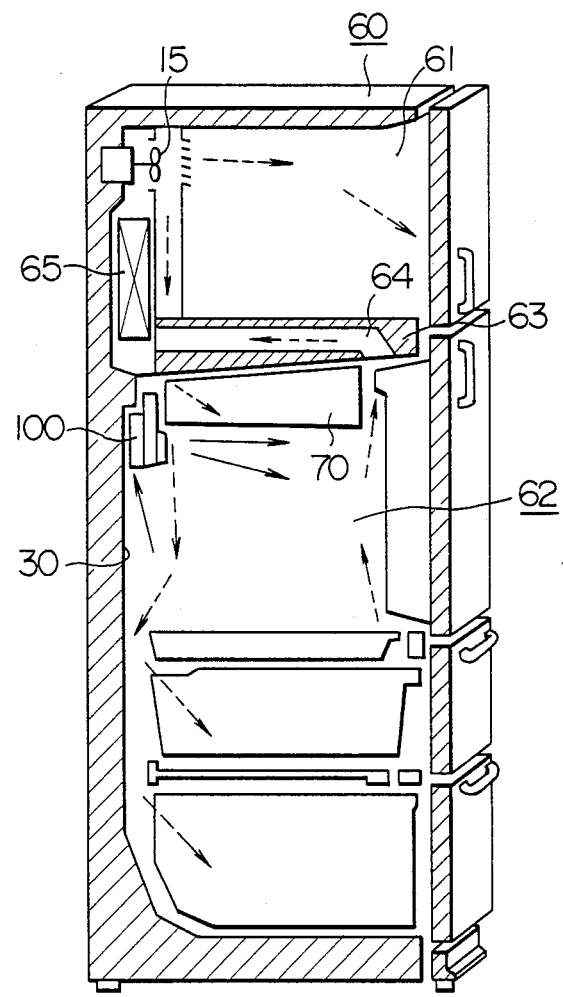
FIG. 18 is a perspective sectional view of an embodiment of a refrigerator incorporating the stink removing apparatus.

FIG. 18 shows an example that the stink removing apparatus shown in FIG. 8 is mounted in the refrigerator 60, where the stink removing apparatus is designated by a reference numeral 100. The apparatus 100 is disposed at an upper portions of a face of an inner rear wall 30 in a refrigerating room 62 of the refrigerator 60. With this arrangement, the flow of air of which stink ingredient is absorbed by the stink removing apparatus 100 will be as shown by solid arrows in FIG. 18. On the other hand, the flow of cold air from a cooler 65 caused by a refrigerator fan 15 disposed in a freezing room 61 of the refrigerator 60 will be as shown by broken arrows in FIG. 18. Since the air of which stink ingredient is absorbed by the apparatus 100 is circulated in the refrigerating room 62, the stink of the whole interior of the refrigerator 60 can be removed.

Figure 19:
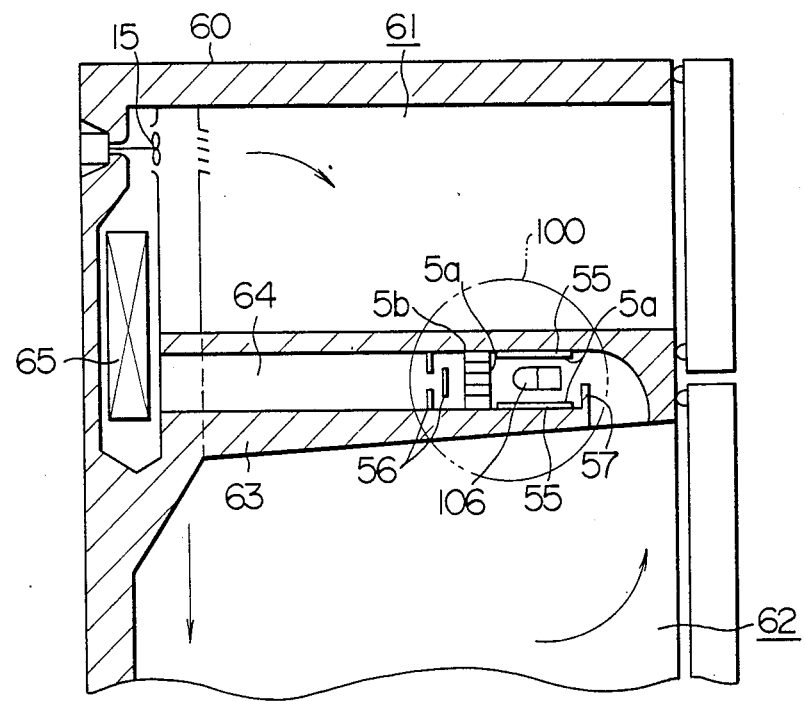
FIG. 19 is a sectional view showing a main portion of the refrigerator incorporating the stink removing apparatus.

Further, in FIG. 18, the refrigerator 60 includes a partition 63 for dividing the freezing room 61 from the refrigerating room 62, which is made of heat-insulating material (for example, urethane) and has a cold air passage 64 formed therein, and a food tray 70. The cooler 65 may be, for example, constituted by cooling pipes and cooling fins disposed between the pipes. While the stink removing apparatus 100 shown in FIG. 18 includes the blower fan 104 (FIG. 20), as shown in FIG. 19, the stink removing apparatus 100 may be constructed by utilizing the blown air from the refrigerator fan 15, such as a construction shown in a broken circle in FIG. 19. In the refrigerator 60 shown in FIG. 19, the cold air generated by the cooler 65 is circulated by the refrigerator fan 15 in the interior of the refrigerator as shown by arrows in FIG. 19. The stink removing apparatus 100 is arranged in the cold air passage 64 formed in the partition 63 for dividing the freezing room 61 from the refrigerating room 62, with the result that the air is passed through the apparatus 100 positively. Consequently, in this case, a separate blower fan for the apparatus 100 can be omitted. The stink removing apparatus 100 comprises a central ultraviolet ray lamp 106 acting as the photocatalyst exciting light source, fibre form active carbon 55 arranged around the lamp, honeycomb active carbon 5, and layers 5a of the photocatalyst formed on each active carbon. Shield plates 56 and 57 for the ultraviolet rays are disposed in an inlet and an outlet of the apparatus, respectively. When the cold air flow is used alone without energizing the ultraviolet ray lamp 106 acting as the photocatalyst exciting source, the stink ingredient is absorbed to each active carbon 5b, 55 to remove stink. When the ultraviolet ray lamp 106 is energized, the photocatalyst layers 5a are in the excited condition, thus creating the decomposition of the stink ingredient as mentioned above, thereby cleaning each active carbon 5b, 55. Incidentally, when the ultraviolet ray lamp 106 is energized while permitting the cold air flow, the stink ingredient in the air flow is simultaneously decomposed while cleaning the active carbon.

As mentioned above, when the stink removing apparatus 100 is constituted by utilizing the air flow caused by the refrigerator fan 15, it is not necessary to dispose or arrange the apparatus 100 in the air passage 64 of the partition 63, but to arrange it at any position where the air flow is created by the fan 15. Further, it should be noted that it is not necessary to arrange the apparatus 100 through the whole cross-sectional area of the air passage 64 in the partition 63 as shown in FIG. 19, but the apparatus 100 can be arranged only in a part of the cross-sectional area of the passage 64.

Figure 20:
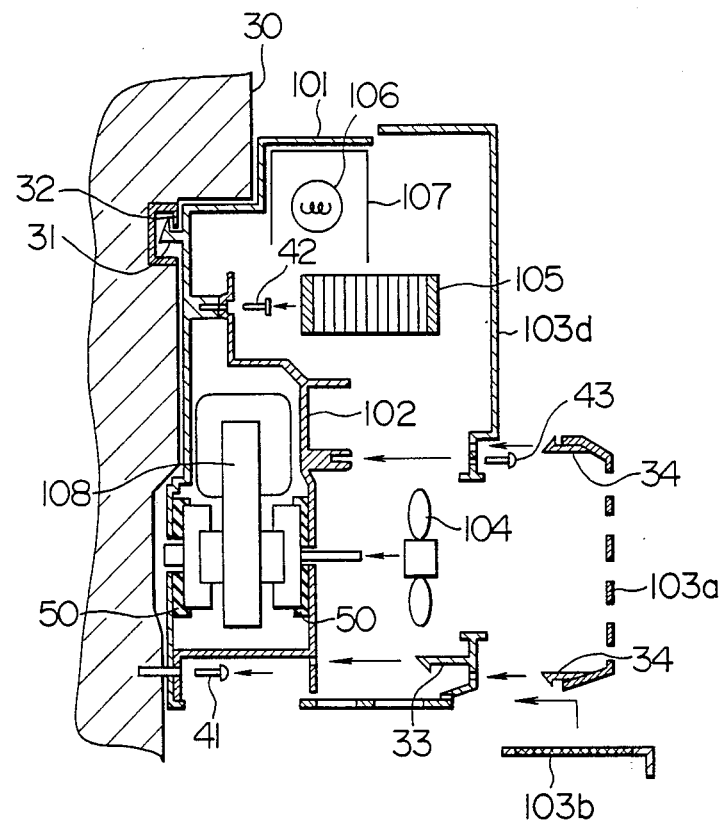
FIG. 20 is a sectional view for explaining how to attach the stink removing apparatus to the refrigerator.

FIG. 20 shows an example of a mounting method for mounting the stink removing apparatus 100 shown in FIG. 18 in the refrigerator. In FIG. 20, first of all, a fan motor 108 is fixed by means of the lower and intermediate covers 101, 102 through rubber seats 50, then the intermediate cover 102 is fixed to the lower cover 101 by means of a setscrew 42 and the above mentioned pawls 52 (of the intermediate cover 102) and receiver openings 51 (of the lower cover). Thereafter, a pawl 31 formed on the outer surface of the lower cover 101 is inserted into a pawl receiver 32 formed in the inner wall 30 of the refrigerator and then the lower and intermediate covers 101, 102 are fixed to the inner wall 30 of the refrigerator by means of setscrews 41. Next, the absorbent 105 and the blower fan 104 are attached to the intermediate cover 102 and the fan motor 108, respectively. Thereafter, the body of the upper cover 103d is mounted on the lower cover 101 and fixed thereto by means of setscrews 43 and the pawl 33. Then, the fan cover 103a is mounted on the upper cover body 103d through the pawl 34, and lastly the pre-filter 103b is inserted into the upper cover body 103d, thus completing the assembling operation. Arrows in FIG. 20 show the assembling directions regarding the associated elements.

Figure 21:
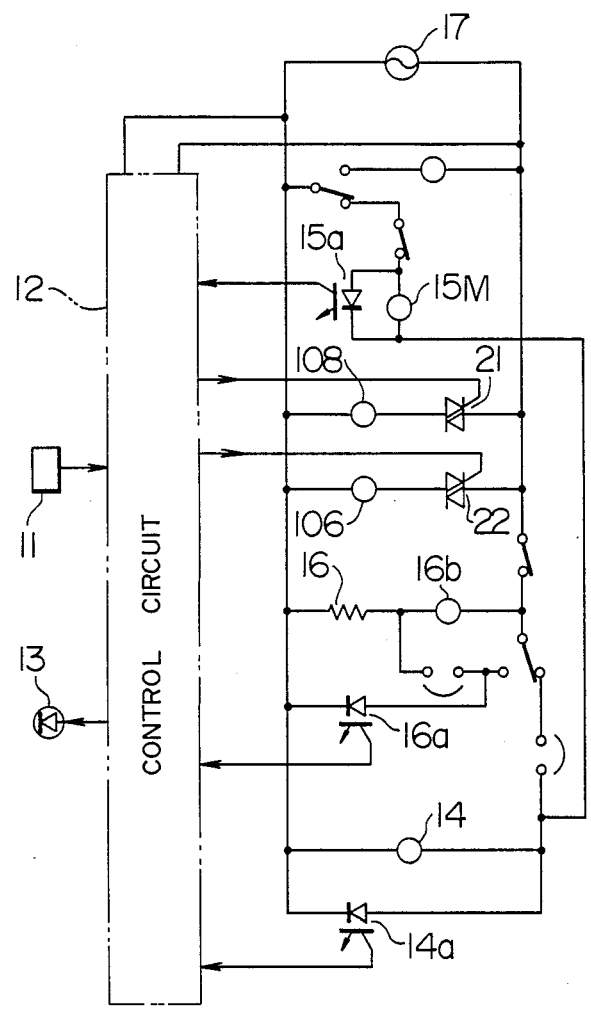
FIG. 21 shows an embodiment of a control circuit for controlling the operation of the refrigerator incorporating the stink removing apparatus.

An example of a control circuit for controlling the stink removing apparatus is shown in FIG. 21. For simplicity's sake of explanation, only the controlling operations required to perform the stink decomposing operation will be explained herebelow. By starting the stink removing apparatus by pushing a starter button 11, the operating command is transmitted to a control circuit 12, thereby operating the stink removing apparatus. When the starter button 11 is depressed, a stink removing operation displaying lamp 13 is illuminated to indicate that the stink removing apparatus being operated.

The motor 108 for the blower fan 104 in the apparatus is controlled by a signal emitted from an operation detector 14a of a compressor 14 in a freezing cycle (not shown) of the refrigerator, thereby energizing a fan motor switch 21 when the compressor 14 is being operated, thus driving the fan motor 108 to remove the stink in the refrigerator. By such operation, the start-stop control for the fan motor is performed, thus preventing the overheat of the fan motor 108 to lengthen its service life. When a door of the refrigerator is opened, a motor 15M for the refrigerator fan 15 is stopped; the opening and closing of the door are detected by a refrigerator fan operation detector 15a, thus stopping the refrigerator fan 15 when the door is being opened, regardless of the operation of the compressor 14. With such arrangement, it is possible to minimize an amount of cold air escaped out of the refrigerator when the door is opened.

Further, a ultraviolet ray lamp 106 is operated and controlled as follows. That is to say, after a defrosting heater 16 is energized to perform the defrosting operation, when disenergization of the defrosting heater 16 which is caused upon completion of the defrosting operation is detected by a defrost detector 16a, the ultraviolet ray lamp 106 is illuminated for a predetermined time interval by energizing a lamp driving switch 22, and at the same time the fan motor 108 is stopped by disenergizing the fan motor switch 21, regardless of the operation of the compressor 14. Accordingly, a defrost timer 16b can also act as a timer for the stink removing apparatus, thus eliminating the necessity of the provision of a separate timer for the apparatus.

After the predetermined time interval is elapsed, the ultraviolet ray lamp 106 is disenergized, and the stink removing operation is continued while controlling the operation of the blower fan of the stink removing apparatus by detecting the operation of the compressor 14 and the opening and closing of the door. When the stink removing operation is not desired, the stink removing apparatus may be stopped by disenergizing the starter button 11. In this case, the displaying lamp 13 will be extinguished. A reference numeral 17 designates a power source.

In this embodiment, normally, the stink removing operation is performed by absorbing the stink ingredient by means of the absorbent 5 while passing the air in the refrigerator through the absorbent by means of the blower fan 104. However, when the blower fan 104 is stopped and the ultraviolet ray lamp 106 is illuminated, the cleaning operation of the absorbent is performed in the following manner. That is to say, the stink ingredient absorbed to the honeycomb form active carbon of the absorbent 105 is floated gradually onto the surface of the active carbon due to the heat from the ultraviolet ray lamp 106. In this case, the photocatalyst disposed on the active carbon will be in the excited condition. Incidentally, as stated above, when the blower fan motor 108 is stopped while the ultraviolet ray lamp 106 being applied, it is possible to effectively contact the stink ingredient floated on the honeycomb form active carbon with the photocatalyst layer without escape. Further, by stopping the blower fan motor 108 for the fan 104, the heat from the ultraviolet ray lamp 106 can effectively be transmitted to the honeycomb form active carbon, thus promoting the floating operation of the stink ingredient toward the surface of the honeycomb form active carbon.

Further, when the density of the stink ingredient in the proximity of the surface of the honeycomb form active carbon is decreased, since the stink ingredient is shifted from inside to outside of the active carbon due to the diffusion, the cleaning operation of the honeycomb form active carbon can be performed more smoothly. The time interval for applying the ultraviolet ray lamp 106 to carry out the cleaning operation may be a time during when the honeycomb form active carbon can decompose the stink ingredient absorbed thereto between from one defrost operation to the next one.

Incidentally, it is preferable that the socket 106a (FIG. 16) is positioned above the ultraviolet ray lamp 106 when installed in the refrigerator so that even if the ultraviolet ray lamp is frosted the water can effectively be prevented from dropping onto the socket which may cause the deterioration of insulating feature of the socket.

Figure 22:
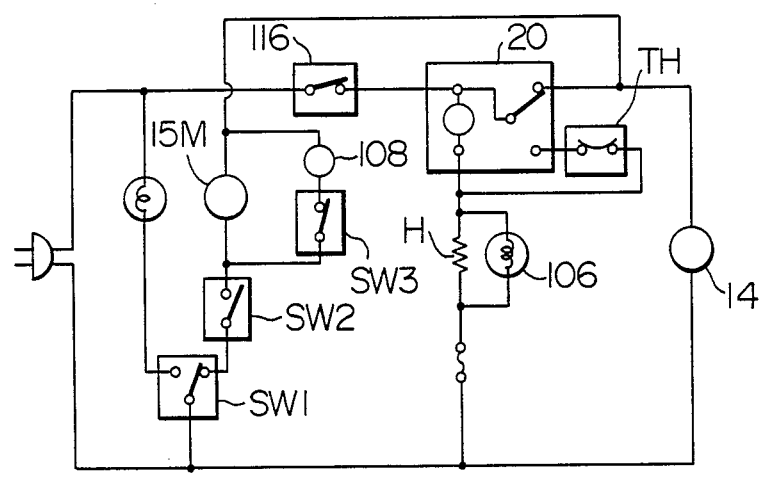
FIG. 22 shows another embodiment of such control circuit.

In the explanation mentioned above, while an example of the stink removing operation controlled by the starter button was described, the present invention is not limited to such example, but can be applied to the case where the exciting light source is energized in synchronous with the defrost of the cooler. FIG. 22 shows an example of a control circuit used in such case. In FIG. 22, the compressor 14 constituting a freezing cycle (not shown) is driven by a temperature regulator 116. The motor 15M for the refrigerator fan is driven in synchronous with the compressor 14. Incidentally, the freezing cycle may include the compressor, cooler, condenser and the like as already known. When a defrost timer 20 for the cooler clocks for a predetermined time, it positively changes over its contacts to supply voltage to a defrost heater H. The lamp 106 is connected in parallel to the heater H and is illuminated during defrosting time (for example, 20-40 minutes). After the defrosting operation is completed, voltage is applied to the defrost timer 20 again by separating contacts of a bimetal thermostat TH, and after a predetermined time period the compressor 14 is activated. In this case, the defrost timer 20 is connected in series to the parallel circuit constituted by the defrost heater H and the lamp 106; however, there arises no problem, since resistance of the defrost heater H is considerably small in comparison with impedance of the defrost timer 20. Door switches SW1 and SW2 associated with the door of the refrigerator are connected in series to the fan motor 15M in such a manner that when the door is opened the fan motor 15M is stopped. When a manual switch SW3 connected in series to the motor 108 for the blower fan 104 is activated, the fan motor 108 is driven in synchronous with the motor 15M. Accordingly, the lamp 106 decomposes the stink ingredient collected to the absorbent while the refrigerator is used, i.e., the compressor 14 is driven, regardless of the ON-OFF operation of the switch SW3.

According to the present invention, a stink removing apparatus for a refrigerator, which maintains the stink removing ability effectively for a long time, can be provided.

What is claimed is:

1. A stink removing apparatus using absorbent, comprising a member in which photocatalyst is applied on a surface of said absorbent for absorbing stink ingredient or as mixed and kneaded with said absorbent, said photocatalyst decomposing the stink ingredient absorbed on said absorbent when excited by light and a light source for exciting said photocatalyst.

2. A stink removing apparatus according to claim 1, wherein said absorbent is formed as a honeycomb form, and said photocatalyst is excited while passing air flow through apertures of the honeycomb form.

3. A stink removing apparatus according to claim 1, wherein said absorbent is formed as a honeycomb form, and the stink ingredient is collected by absorbing it to said absorbent while passing air flow through apertures of the honeycomb form, and said photocatalyst is intermittently excited.

4. A stink removing apparatus according to claim 1, wherein said absorbent comprises simple substance or composite of active carbon, zeolite, porous ceramics or silica gel.

5. A stink removing apparatus according to claim 1, wherein said photocatalyst comprises simple substance or composite of metallic oxide such as titanium oxide, tungsten oxide, zinc oxide and the like.

6. A stink removing apparatus according to claim 1, wherein the photocatalyst having a particle diameter sufficiently larger than pores in said absorbent is applied to the surface of said absorbent.

7. A stink removing apparatus according to claim 1, wherein said exciting source is arranged in the proximity of a high absorbing density area of said absorbent.

* * * * *